(12) United States Patent
Tsou et al.

(10) Patent No.: US 6,734,427 B1
(45) Date of Patent: May 11, 2004

(54) TEM/SEM SAMPLE PREPARATION

(75) Inventors: Yun-Ming Tsou, Chu-Pei (TW);
Wen-Chun Chen, Taipei (TW);
Wen-Tung Chang, Hsin-Chu (TW)

(73) Assignee: United Microelectronics Corp.,
Hsin-Chu (TW)

( * ) Notice: Subject to any disclaimer, the term of this patent is extended or adjusted under 35 U.S.C. 154(b) by 0 days.

(21) Appl. No.: 10/248,746

(22) Filed: Feb. 14, 2003

(51) Int. Cl.[7] ................................................. H01J 37/20
(52) U.S. Cl. ............. 250/307; 250/442.11; 250/440.11; 438/691; 438/592; 438/593; 438/693; 451/41; 750/309; 750/307; 750/311
(58) Field of Search ........................... 250/307, 442.11, 250/440.11; 438/691, 592, 593, 693; 451/41; 750/309, 307, 311

(56) References Cited

U.S. PATENT DOCUMENTS 5,741,171 A * 4/1998 Sarfaty et al. ................. 451/6
6,042,736 A * 3/2000 Chung .......................... 216/33
6,538,254 B1 * 3/2003 Tomimatsu et al. ..... 250/442.11

* cited by examiner

Primary Examiner—John R. Lee
Assistant Examiner—Zia R. Hashmi
(74) Attorney, Agent, or Firm—Winston Hsu

(57) ABSTRACT

A method of preparing a test sample for electron microscopy analysis is disclosed. First, a chip segment is attached to a holder of a sample polisher, and a first polishing end of the chip segment is polished by using the sample polisher to generate a first polished cross section. Thereafter, the chip segment is detached from the holder. Further, a carrier segment is attached to the first cross section of the chip segment and the conjoined carrier segment and the chip segment are attached to a pad segment so as to form a stacked structure. Finally, the stacked structure is attached to the holder, and a second polishing end of the chip segment is polished to generate a second polished cross section.

21 Claims, 7 Drawing Sheets

TEM/SEM SAMPLE PREPARATION

BACKGROUND OF THE INVENTION

1. Field of the Invention

The present invention relates to the field of failure analysis in semiconductor processes, and more particularly, to electron microscopy sample preparation without using a polishing tool, so as to reduce sample preparation costs and time.

2. Description of the Prior Art

As IC technology progresses, electron microscopy is used extensively in failure analysis, especially the transmission electron microscope (TEM). According to the signal obtained from the interaction of particles and electrons, the information to be analyzed by the TEM can be divided into three parts: 1. The displayed image gathered by the transmitted electron or the elastic scattering electron, 2. The electron diffusion pattern (DP) formed for researching tiny tissues and crystal structures, and 3. The chemical composition analysis obtained by using the energy dispersive spectrometer (EDS) or the electron energy loss spectroscopy (EELS). With the improvement of instruments, the analytical electron microscope and the high resolution electron microscope can be combined together to display images. With this combination, the nano beam diffraction (NBD) and the convergent beam diffraction (CBD) can be done. It has various abilities to satisfy analytical demands in various ranges.

The TEM instrument system mainly comprises: 1. An electron gun that is one of three types a tungsten filaments electron gun, a $LaB_6$ electron gun, and a field emission electron gun (similar to a scanning electron microscope (SEM)), 2. An electromagnetic lens system that includes a condenser lens, an objective lens, an intermediate lens, and a projective lens, 3. A sample chamber having a sample holder of that is either a side entry type or a top entry type, and 4. An image observation and record system comprising a ZnS/CdS coating fluorescence screen or a photonegative one.

The observation mode of the TEM has two types: a planar observation mode and a cross-section observation mode. In the planar observation mode, electron beams are emitted toward a chip surface vertically to make the right side observation, which is usually for researching the device layout, the materials, or the size measurement. In the cross-section observation mode, a vertical structure of the chip is sideling observed, and it is usually for measuring each layers thickness, researching the material stacked frame, and observing the interface structure. The sample preparation relates to the observation mode. There are two methods of cutting and trimming the sample when observing a routine procedure. The planar observation mode utilizes a chemical solution etching process and the cross-section observation mode utilizes an ion miller to cut and trim the sample. However, the planar observation mode can utilize the ion miller and the cross-section observation mode can utilize a focus ion beam (FIB) to cut and trim the sample for a more precise observation. The FIB allows a lateral orientation on the sample so that the cross-section can be prepared in a selected area, at least within certain boundaries, of the portion of the sample to be analyzed.

The conventional transmission electron microscopy has several limitations including: 1. The thickness of the sample has to be below 3 millimeters (mm), 2. The most ideal observation thickness of the sample is about 500~1000 angstroms (Å) due to the limitation of the transmission electron beam, 3. The dimension of the observation region is usually below 100 mm due to the difficulty of sample preparation, and 4. In some situations, such as the chip sealing, the cross-section analysis of the single bit failure, or the cross-section analysis of single contact hole, the sample preparation is very difficult, thereby reducing the usefulness of the sample preparation.

In addition, when utilizing a conventional sample polisher such as a Sagitta's NEXT-1 automatic polisher to prepare the sample, a particular tool manufactured by the polisher factory has to be used in the sample preparation. The particular tool cannot be recycled and has to be molded by itself so as to increase costs of the sample preparation, and more analysis time is needed when using the particular tool to prepare the sample.

SUMMARY OF THE INVENTION

It is therefore a primary objective of the claimed invention to provide a novel electron microscope sample preparation without the particular tool to allow relatively fast sample preparation and cost reductions.

According to the claimed invention, a TEM sample preparation is disclosed. A sample polisher including a holder and a chip segment to be tested having a first polishing end, a second polishing end, and a pre-selected testing point between the first polishing end and second polishing end are provided. The chip segment is attached to the holder of the sample polisher, and the first polishing end of the chip segment is polished by using the sample polisher to generate a first polished cross section. The chip segment has a first predetermined distance between the first cross section and the testing point. The chip segment is detached from the holder. A carrier segment is attached to the first cross section of the chip segment. The conjoined carrier segment and the chip segment are attached to a pad segment so as to form a stacked structure. The stacked structure is attached to the holder, and the second polishing end of the chip segment is polished to generate a second polished cross section by using the sample polisher. The chip segment has a second predetermined distance between the second polished cross section and the testing point.

The claimed invention prepares the sample without utilizing the conventional particular tool so as to allow relatively fast sample preparation and cost reduction simultaneously.

These and other objectives of the present invention will no doubt become obvious to those of ordinary skill in the art after reading the following detailed description of the preferred embodiment that is illustrated in the various figures and drawings.

DETAILED DESCRIPTION

Please refer to FIG. 1 through FIG. 6. FIG. 1 through FIG. 6 are amplified-side views of a method of preparing a sample for an electron microscopy according to the present invention. The electron microscope is the SEM or the TEM, and the sample is suitable for a cross-section observation mode.

In the preferred embodiment of the present invention, the sample preparation is performed in a Sagitta's NEXT-1 automatic machine. The Sagitta's NEXT-1 automatic machine includes a polishing pad and at least one holder for attaching a sample to be polished or a polishing semi-manufactured sample. Since the Sagitta's NEXT-1 automatic machine is in common use for IC failure analysis in this industry, its structure and operating theorem give unnecessary details, and will not be discussed. U.S. Pat. No. 5,741,171 "Precision Polishing System" discloses the operating theorem of the Sagitta's NEXT-1 automatic machine.

Figure 1:
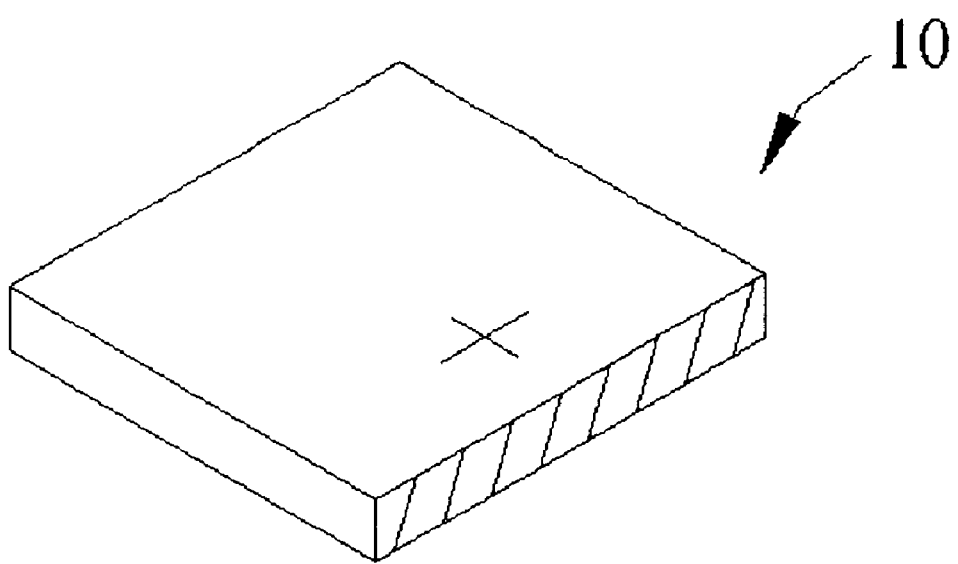
FIG. 1 through FIG. 6 are side-amplified views illustrating electron microscope sample preparation according to the present invention.
Figure 2:
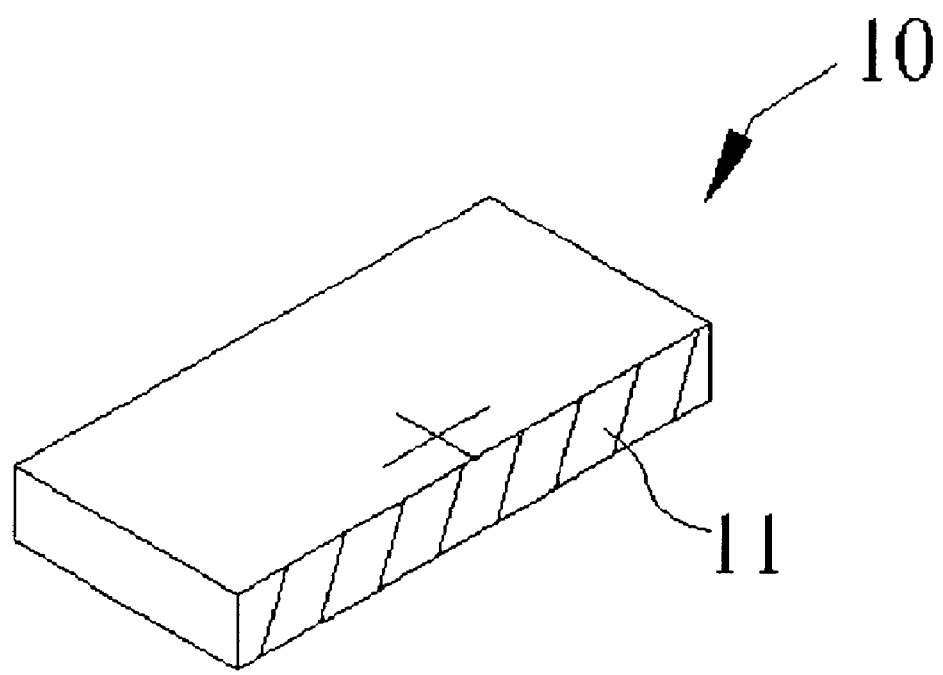
Figure 7:
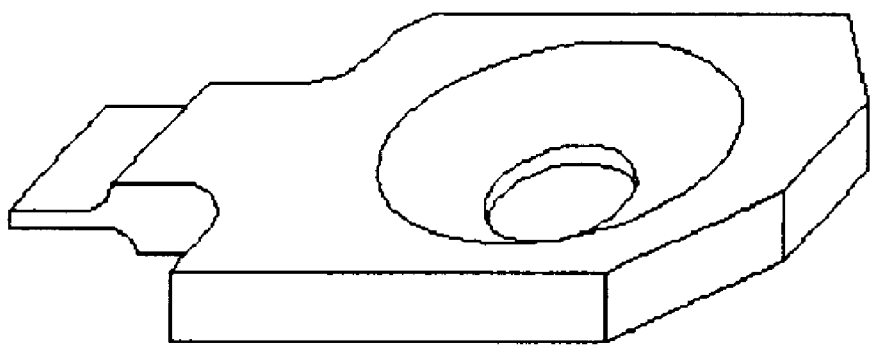
FIG. 7 is a schematic diagram illustrating a conventional particular tool.

Referring to FIG. 1, before polishing, a chip to be tested is pre-cut into a sample 10 with a dimension of about 1 centimeter (cm)×1 cm. A cross center shown in FIG. 1 is a pre-selected testing point. First, the sample 10 is attached to a specimen holder of the Sagitta's NEXT-1 automatic polisher by using hot melted glue. Then the sample 10 is polished by using the Sagitta's NEXT-1 automatic polisher until a first polishing end of the sample 10 distances from the cross center by about 5~10 micrometers ($\mu$m), so as to generate a first polished cross section 11 shown in FIG. 2. This means that the sample 10 has a distance of about 5~10 $\mu$m between the first polished cross section 11 and the testing point. Further, the sample 10 is detached from the holder by heating, as shown in FIG. 2. The heating temperature is about 40~60° C. In the conventional method, the polished sample 10 will be attached to the particular tool shown in FIG. 7, and then the conjoined sample will be polished to a desired thickness. As mentioned above, the particular tool is a waste material that increases costs of preparing the sample.

Figure 3:
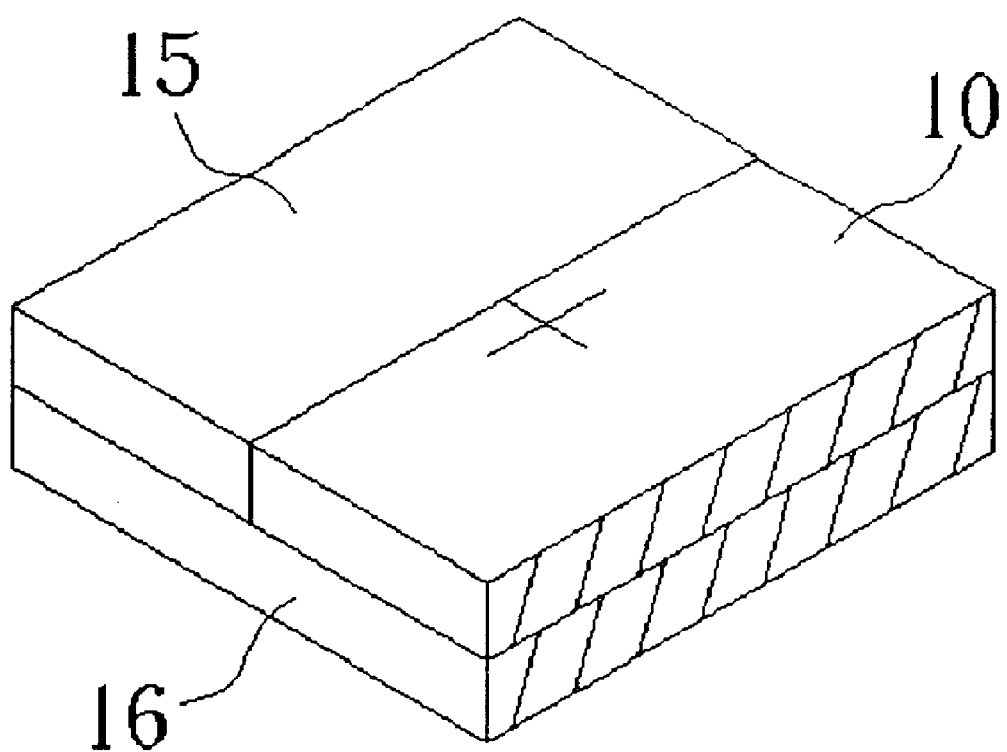

Therefore, the present invention does not use the particular tool, a tool holder, and the conventional sample preparation method and develops another simple method for preparing the sample. Referring to FIG. 3, after the sample 10 is detached from the holder by heating, a carrier segment 15 is attached to the first cross section 11 of the sample 10 by using hot melt glue such as hot wax without attaching the sample 10 to the particular tool. Further, the conjoined carrier segment 15 and the sample 10 are attached to a pad segment 16 by using hot melt glue so as to form a stacked structure. The carrier segment 15 and the pad segment 16 are dummy wafer segments. In addition, the carrier segment 15 and the pad segment 16 are other nonmetallic materials, such as glass or other materials which have a polishing rate approximately to the sample 10.

Figure 4:
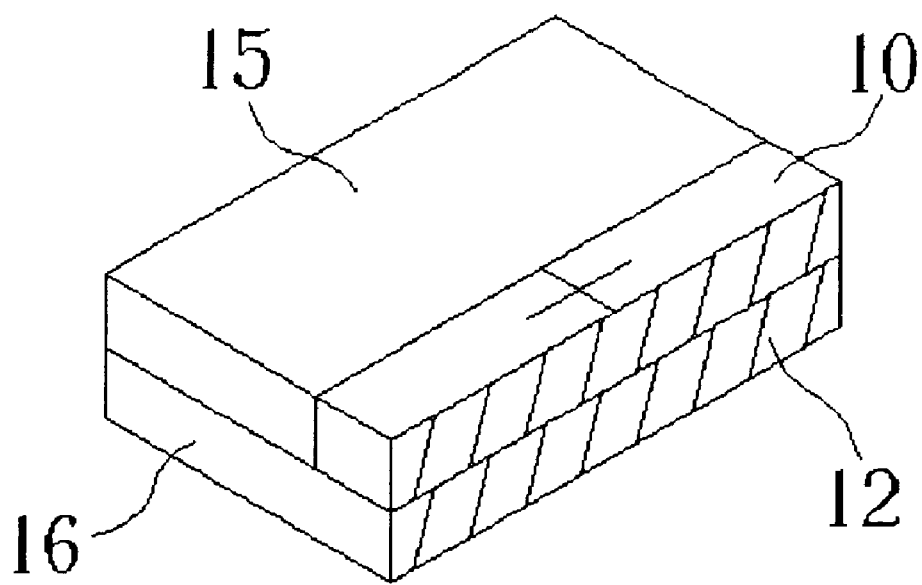

Until the hot melt glue coagulates, the stacked structure is attached to the above-mentioned holder by using hot melt glue. Then the stacked structure is polished by using the Sagitta's NEXT-1 automatic polisher until a second polishing end of the stacked structure distances from the testing point by about 5~10 $\mu$m so as to generate a second polished cross section 12. At this time, the sample 10 has a thickness, namely a distance between the first polished cross section 11 and the second polished cross section 12, of about 10~20 $\mu$m. The thickness can be adjusted if desired. Finally, the polished sample 10, the carrier segment 15, and the pad segment 16 are detached from the holder as shown in FIG. 4.

Figure 5:
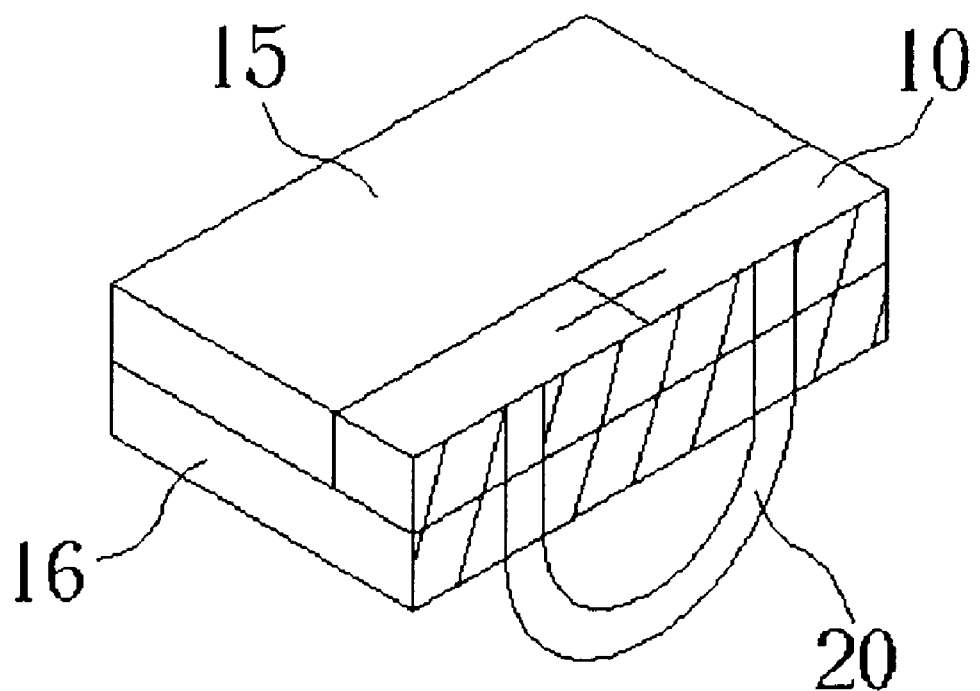
Figure 6:
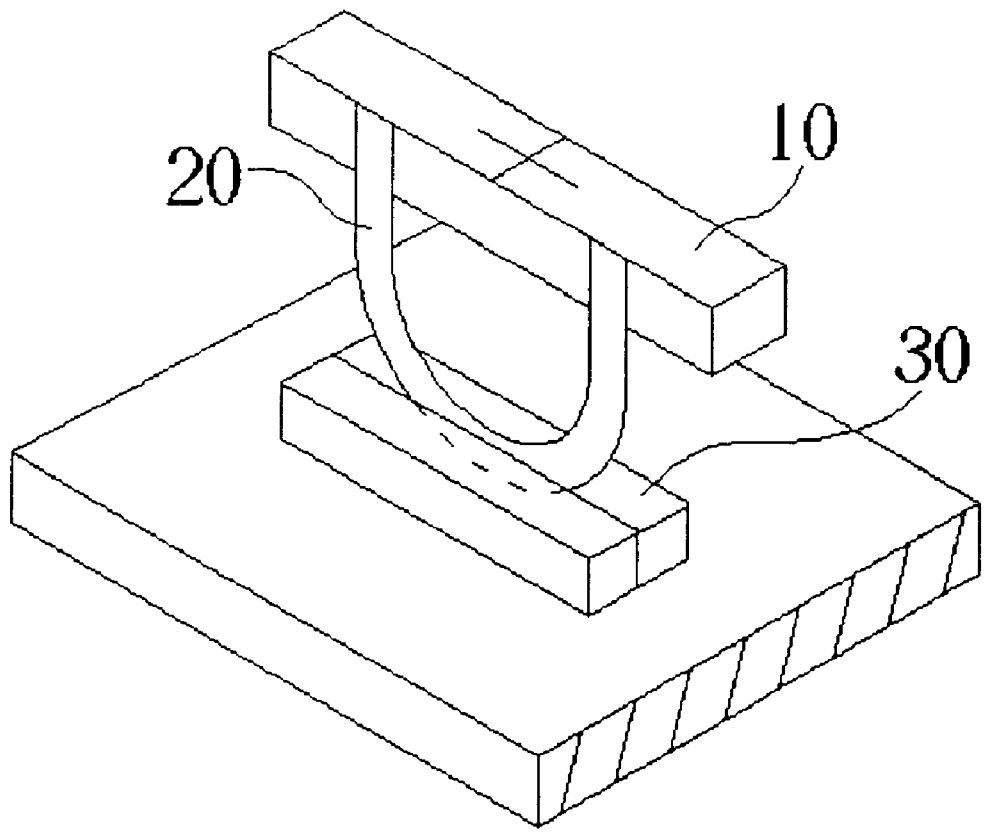

Referring to FIG. 5, a copper metal ring 20 is attached to the second polished cross section 12 by using AB glue or fast curing glue. Care must be taken so that the AB glue or the fast curing glue can be smeared over the second polished cross section 12 so that the metal ring 20 can be mounted on the sample 10. After the AB glue or the fast curing glue coagulates, the sample 10 with the metal ring 20 thereon is detached from the stacked structure by using acetone or heating. Finally, as shown in FIG. 6, the metal ring 20 is fixed on a base 30 in an upright manner and the sample 10 preparations for the FIB are completed, with the subsequent process is omitted.

The electron microscope sample preparation of the present invention categorizes six steps:

Step 1: A chip segment of a wafer to be tested is pre-cut into a sample with dimensions of about 1 centimeter (cm)×1 cm, and then the sample is attached to a holder of a Sagitta's NEXT-1 automatic polisher.

Step 2: The sample is polished using the Sagitta's NEXT-1 automatic polisher until a first polishing end of the sample distances from a testing point by about 5~10 $\mu$m, and then the sample is detached from the holder by heating.

Step 3: A polished cross section of the sample is attached to a dummy wafer segment using hot melt glue, and then the sample is attached to a wafer pad segment.

Step 4: The stacked sample is attached to the holder of the Sagitta's NEXT-1 automatic polisher, and then the stacked sample is polished until a second polishing end of the stacked sample distances from the testing point by about 5~10 $\mu$m, and the stacked sample is detached from the holder.

Step 5: A copper metal ring is attached to the sample by using AB glue and then the sample is detached from the dummy wafer segment and the wafer pad segment by heating or other methods.

Step 6: The copper metal ring fixed on the sample and the copper metal ring is attached to a dummy wafer base in an upright manner by using hot melt glue to perform cutting and trimming by the FIB.

In briefly speaking, the above-mentioned step 3 to step 5 of the present invention are different from the conventional method. The present invention utilizes the carrier segment 15 and the pad segment 16 to replace the conventional particular tool so as to allow relatively fast sample preparation and reduce costs.

Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A method of preparing a test sample for electron microscopy analysis, comprising:

providing a sample polisher comprising a holder;

providing a chip segment to be tested having a first polishing end, a second polishing end, and a pre-selected testing point between the first polishing end and second polishing end;

attaching the chip segment to be tested to the holder;

polishing the first polishing end of the chip segment by using the sample polisher to generate a first polished cross section, wherein the chip segment to be tested has a first predetermined distance between the first cross section and the testing point;

detaching the chip segment to be tested from the holder;

attaching a carrier segment to the first cross section of the chip segment to be tested;

attaching the conjoined carrier segment and the chip segment to be tested to a pad segment so as to form a stacked structure;

attaching the stacked structure to the holder; and polishing the second polishing end of the chip segment to be tested to generate a second polished cross section, wherein the chip segment to be tested has a second predetermined distance between the second polished cross section and the testing point.

2. The method of claim 1 wherein dimensions of the chip segment to be tested are about 1 cm×1 cm before polishing.

3. The method of claim 1 wherein the sample polisher is Sagitta's NEXT-1 automatic polisher.

4. The method of claim 1 wherein the first predetermined distance is about 5~10 micrometers.

5. The method of claim 1 wherein the second predetermined distance is about 5~10 micrometers.

6. The method of claim 1 wherein the chip segment to be tested is attached to the holder by using hot melt glue.

7. The method of claim 1 wherein the carrier segment is attached to the first polished cross section by using hot melt glue.

8. The method of claim 1 wherein the carrier segment is a dummy wafer segment.

9. The method of claim 1 wherein the pad segment is a dummy wafer segment.

10. A method for preparing a TEM sample, comprising:

providing a sample polisher comprising a holder;

providing a chip segment to be tested having a first polishing end, a second polishing end, and a pre-selected testing point between the first polishing end and second polishing end;

attaching the chip segment to be tested to the holder;

polishing the first polishing end of the chip segment by using the sample polisher to generate a first polished cross section, wherein the chip segment to be tested has a first predetermined distance between the first cross section and the testing point;

detaching the chip segment to be tested from the holder;

attaching a carrier segment to the first cross section of the chip segment to be tested;

attaching the conjoined carrier segment and the chip segment to be tested to a pad segment so as to form a stacked structure;

attaching the stacked structure to the holder;

polishing the second polishing end of the chip segment to be tested to generate a second polished cross section, wherein the chip segment to be tested has a second predetermined distance between the second polished cross section and the testing point;

attaching a metal ring to the second polished cross section; and detaching the chip segment to be tested with the metal ring thereon from the stacked structure.

11. The method of claim 10 wherein dimensions of the chip segment to be tested are about 1 cm×1 cm before polished.

12. The method of claim 10 wherein the sample polisher is Sagitta"s"s NEXT-1 automatic polisher.

13. The method of claim 10 wherein the first predetermined distance is about 5~10 micrometers.

14. The method of claim 10 wherein the second predetermined distance is about 5~10 micrometers.

15. The method of claim 10 wherein the chip segment to be tested is attached to the holder by using hot melt glue.

16. The method of claim 10 wherein the carrier segment is attached to the first polished cross section by using hot melt glue.

17. The method of claim 10 wherein the carrier segment is a dummy wafer segment.

18. The method of claim 10 wherein the pad segment is a dummy wafer segment.

19. The method of claim 10 wherein the metal ring is made of copper.

20. The method of claim 10 wherein the metal ring is attached to the second polished cross section by using fast curing glue.

21. The method of claim 10 wherein the chip segment to be tested is detached from the stacked structure by using acetone or heating.

* * * * *